(12) United States Patent
Tognarelli et al.

(10) Patent No.: US 8,186,875 B2
(45) Date of Patent: May 29, 2012

(54) METHOD FOR DETERMINING REHEAT CRACKING SUSCEPTIBILITY

(75) Inventors: Leonardo Tognarelli, Florence (IT); Eugenio Giorni, Florence (IT); Marco Romanelli, Florence (IT); Marco Manetti, Florence (IT)

(73) Assignee: Nuovo Pignone S.p.A., Firenze (IT)

( * ) Notice: Subject to any disclaimer, the term of this patent is extended or adjusted under 35 U.S.C. 154(b) by 736 days.

(21) Appl. No.: 12/329,744

(22) Filed: Dec. 8, 2008

(65) Prior Publication Data

US 2010/0070203 A1   Mar. 18, 2010

Related U.S. Application Data

(60) Provisional application No. 61/096,463, filed on Sep. 14, 2008, provisional application No. 61/096,926, filed on Sep. 15, 2008.

(51) Int. Cl.
*G01N 25/00* (2006.01)
(52) U.S. Cl. ............................................. 374/46; 374/50
(58) Field of Classification Search .................... 374/46, 374/50, 57, 5
See application file for complete search history.

(56) References Cited

U.S. PATENT DOCUMENTS

| | | | | |
|---|---|---|---|---|
| 3,350,917 | A * | 11/1967 | Wincklhofer et al. | 374/50 |
| 5,201,582 | A * | 4/1993 | Lesniak | 374/45 |
| 5,567,051 | A * | 10/1996 | Annati et al. | 374/57 |
| 5,746,512 | A * | 5/1998 | Yao et al. | 374/45 |
| 6,146,013 | A * | 11/2000 | Huetter et al. | 374/46 |
| 6,260,998 | B1 * | 7/2001 | Garfinkel et al. | 374/57 |
| 6,776,520 | B2 * | 8/2004 | Zhu | 374/55 |
| 6,860,633 | B2 * | 3/2005 | Davis et al. | 374/55 |
| 7,025,498 | B2 * | 4/2006 | del Puerto | 374/44 |
| 7,083,327 | B1 * | 8/2006 | Shepard | 374/46 |
| 7,287,902 | B2 * | 10/2007 | Safai et al. | 374/5 |
| 7,690,840 | B2 * | 4/2010 | Zombo et al. | 374/121 |
| 7,978,342 | B2 * | 7/2011 | Fakhruddin | 374/55 |
| 7,980,757 | B2 * | 7/2011 | Lai et al. | 374/5 |
| 2004/0134280 | A1 * | 7/2004 | Hedberg et al. | 73/579 |
| 2006/0146907 | A1 * | 7/2006 | Saka et al. | 374/5 |
| 2006/0274812 | A1 * | 12/2006 | Safai et al. | 374/5 |
| 2009/0135879 | A1 * | 5/2009 | Koons et al. | 374/47 |
| 2009/0312956 | A1 * | 12/2009 | Zombo et al. | 374/4 |
| 2010/0070203 | A1 * | 3/2010 | Tognarelli et al. | 702/35 |

* cited by examiner

*Primary Examiner* — Yaritza Guadalupe-McCall
(74) *Attorney, Agent, or Firm* — Potomac Patent Group PLLC

(57) ABSTRACT

System, computer software and method for determining a susceptibility to reheat cracking of a sample of material, which includes a welded area. The method includes measuring a length of the sample, applying a first stress to the sample to achieve a predetermined elongation of the sample, exposing the elongated sample to a predefined heat treatment, applying a second stress to the sample until the sample breaks at least into two different pieces, and determining the susceptibility of the broken sample to reheat cracking.

20 Claims, 20 Drawing Sheets

METHOD FOR DETERMINING REHEAT CRACKING SUSCEPTIBILITY

RELATED APPLICATION

This application is related to, and claims priority from, U.S. Provisional Patent Application Ser. No. 61/096,463, filed on Sep. 14, 2008, and U.S. Provisional Patent Application Ser. No. 61/096,926, filed on Sep. 15, 2008, each entitled "Method for determining reheat cracking susceptibility" and authored by L. Tognarelli et al., the entire disclosures of which are incorporated here by reference.

TECHNICAL FIELD

The present invention generally relates to systems and methods and, more particularly, to mechanisms and techniques for determining reheat cracking susceptibility in a material.

BACKGROUND

In the refining and petrochemical industry, various applications require the usage of high temperatures and pressures inside a reactor for either removing the sulfur or achieving other desired chemical reactions. Thus, the walls of the reactor have to withstand not only to the damaging characteristics of the chemicals inside the reactor but also to the changing conditions, i.e., temperature, pressure, etc. Special materials are used to build the reactors' walls, like stainless steel that includes various alloys.

For the past years, conventional low-alloy chromium-molybdenum 2.25 Cr-1 Mo steel has been extensively used for the reactor vessels. The reactors generally have been operated at temperature lower than 450° C. and with hydrogen partial pressure above 10 MPa. Growing demands for higher service temperatures/pressures imposed an increase of the reactor size, generating problems related to the construction, transportation and high temperature hydrogen attack during the reactor's service.

In order to solve at least this last problem, new generation of Vanadium modified Cr—Mo steel was developed and Nuovo Pignone (a business unit of General Electric located in Florence, Italy) fabricated the first 2.25 Cr 1 Mo 0.25V reactor for the petrochemical industry that withstands high temperatures and hydrogen pressures. This reactor has a wall thickness in excess of 250 mm, a diameter of up to 6 m, lengths up to 60 m, and a weight up to 2000 tons. FIG. 1 shows such a reactor 10. The reactor may be operated in high-temperature high-pressure hydrogen atmosphere. For efficiently carrying out, for example, the desulfurization reaction, the service temperature and pressure are increased, causing an increase in thickness and an overall scale up of the reactor dimensions. Thus, large parts 12 and 14 of the reactor 10 have to be welded together at joint regions 20.

The material (2.25 Cr 1 Mo 0.25V) of the walls of the reactor is used because it exhibits appropriate properties for hydrogen embrittlement, high temperature hydrogen attack and overlay disbonding, good toughness at low temperatures and improved resistance to temper embrittlement.

Because of the large size of the reactor, many parts making up the walls of the reactor have to be welded together as shown in FIG. 1. The welding process induces residual stresses in the joint areas due to the heat produced during this type of process, and the stresses are increased by high wall thickness.

FIG. 2 shows a closer view of a welded region 30, which includes parts 12 and 14 jointed together at the welding region 20. Those regions of the parts 12 and 14, whose properties are affected by the heat generated during the welding process are called heat affected zones (HAZ) and are indicated as regions 22 and 24. Thus, the heat-affected zone is the areas 22 and 24 of the base material that had its microstructure and properties altered by welding. The heat from the welding process and subsequent re-cooling causes this change in the area surrounding the weld. The extent and magnitude of the change in properties depend primarily on the base material, the weld filler metal, and the amount and concentration of heat input during the welding process. To mitigate the stress induced during the welding process stress relieving heat treatments may be applied as indicated by American Petroleum Institute (API), American Society for Testing and Materials (ASTM), and American Society of Mechanical Engineers (ASME).

Combining (i) the residual stress formed during welding inside the walls of the reactor with (ii) the stress relieving heat treatment, results in the appearance of reheat cracking phenomena. Reheat cracking phenomena occurs primarily during the application of the heat treatment noted above, for example, in region 20 of FIG. 2. The reheat cracking occurs when grains at the boundary regions, during elevated temperatures, exhibit less or slightly weaker ductile properties than the grain located away from the boundary regions (creep failure damage mechanism).

Various tests exist for measuring the severity of the reheat cracking. One such test is the Geeble test, which provides qualitative indications about the ductility of a given structure. This test is based on the idea that the region most susceptible to hot cracking is the HAZ zone of the parent metal, in which contaminants entrapped at grain boundaries form liquid or low strength solid films while the grains become stiff and strong. It was also found that if such weak films exist over a large temperature range after solidification, the welded materials show hot cracks in the HAZ zone. To determine the range at which the welded HAZ zone is prone to hot cracking, a concept of nil strength temperature was introduced as the higher temperature of the brittle range, and appropriate attachments were designed to measure it. The lower temperature of the brittle range, so-called nil ductility temperature, was then taken as that at which 5% reduction in area on hot tensile samples appeared.

The Gleeble testing procedure requires a large number of samples to be hot tensile tested with strain rates representative of various welding methods (heat inputs). Thus, a simpler test, the Varestraint test was proposed and applied to study the hot cracking susceptibility of welded alloys. The Varestraint test includes bending a test plate while the weld bead is being made on the long axis of the plate. The original Varestraint test had some limitations, e.g., difficulty in controlling the real amount of strain at the outer bent surface due to the position of a neutral bending axis, which varied depending on the strength and strain partitioning between the hot and cold parts of the sample during bending.

However, the above discussed tests and others suffer from the fact that they provide only qualitative results and not selective responses of the damage causes, i.e., these tests are not able to reproduce the real heat treatments (in terms of time, temperatures and stress) that are used during fabrication.

Although these qualitative tests have been able in the past to ensure the quality of the fabrication processes, recent developments in Europe indicate that reheat cracking problems are surfacing for the 2.25 Cr 1 Mo 0.25V reactors and the existing tests are not enough anymore. Thus, it is desirable to support the manufacturing process of real components with a test method able to determine quantitatively, and not only qualitatively, the extension of the reheat cracking.

Accordingly, it would be desirable to provide systems and methods that are able to overcome the above noted limitations and provide tests for determining the susceptibility of a material to exhibit reheat cracks.

SUMMARY

According to an exemplary embodiment, there is a method for determining a susceptibility of a sample of at least one material, which includes a welded area, to reheat cracking. The method includes measuring a length of the sample; applying a first stress to the sample to achieve a predetermined elongation of the sample; exposing the elongated sample to a predefined heat treatment; applying a second stress to the sample until the sample breaks at least into two different pieces; and determining the susceptibility of the broken sample to reheat cracking.

According to another exemplary embodiment, there is a system for determining a susceptibility of a sample of at least one material, which includes a welded area, to reheat cracking. The system includes an interface configured to, receive first data from a length measuring device that measures a length of the sample, receive second data from a stress applying and measuring device configured to apply a first stress to the sample to achieve a predetermined elongation of the sample and to determine a stress in the sample, receive third data from a heat applying device configured to expose the elongated sample to a predefined heat treatment, and receive fourth data from the stress applying and measuring device configured to apply a second stress to the sample until the sample breaks at least into two different pieces. The system also includes a processor connected to the interface and configured to control the length measuring device, the stress applying and measuring device, and the heat applying device and also configured to determine, based on information received from the length measuring device, the stress applying and measuring device, and the heat applying device the susceptibility of the broken sample to reheat cracking.

According to still another exemplary embodiment, there is a computer readable medium for storing computer executable instructions, wherein the instructions, when executed by a processor, determine the processor to determine a susceptibility of a sample of at least one material, which includes a welded area, to reheat cracking. The instructions include measuring a length of the sample; applying a first stress to the sample to achieve a predetermined elongation of the sample; exposing the elongated sample to a predefined heat treatment; applying a second stress to the sample until the sample breaks at least into two different pieces; and determining the susceptibility of the broken sample to reheat cracking.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

Figure 1:
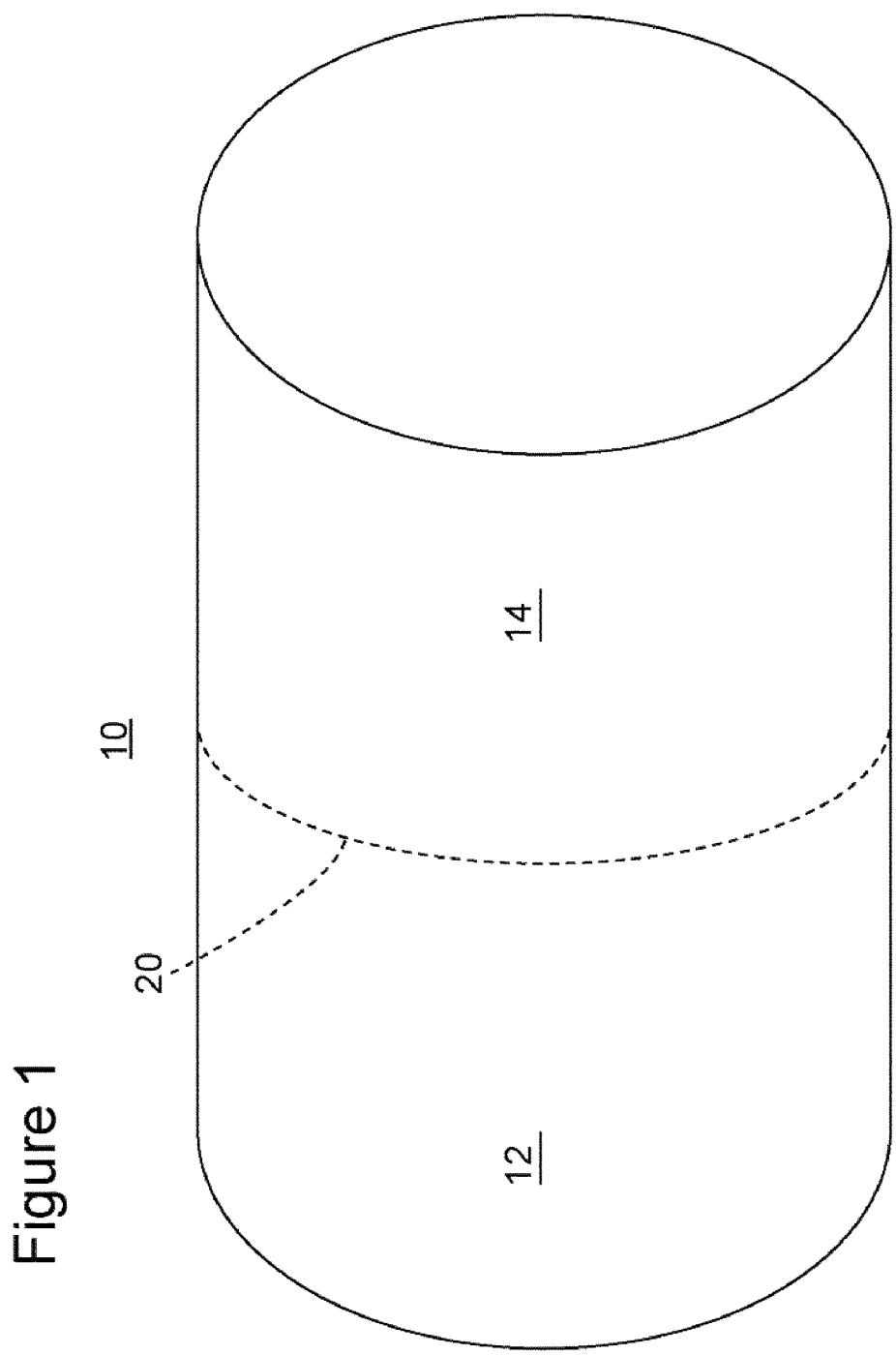
FIG. 1 is a schematic diagram of a reactor.
Figure 2:
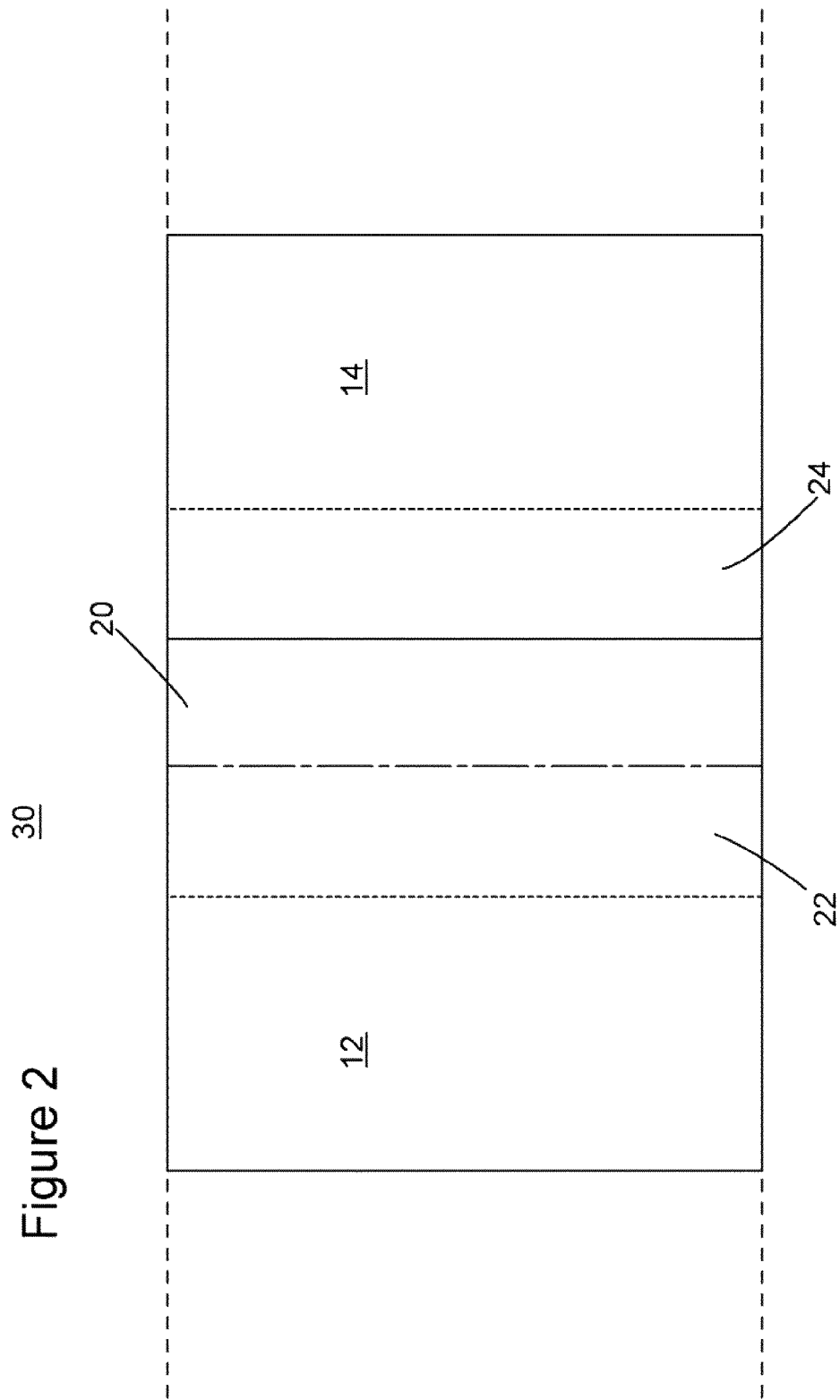
FIG. 2 is a schematic diagram of two welded parts of the reactor of FIG. 1.

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of a chemical reactor. However, the embodiments to be discussed next are not limited to this reactor but may be applied to other reactors or welded parts.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The Reheat Cracking damage was detected in welded joints for various reactors, e.g., hydrocracking reactors. These reactors are characterized by heavy walls with thick welds. These joints are manufactured, for example, by Submerged Arc Welding (SAW) method using the base material 2.25 Cr 1 Mo 0.25V. Reheat cracking flaw nucleate during the heat treatment of the reactors in the temperature range of 600-800° C.

Currently, there is not known a viable or effective way to mitigate this risk. The following exemplary embodiments present test procedures able to provide qualitative data on crack nucleation, which supports real components production without impacting on lead time. Thus, according to an exemplary embodiment, the proposed test method is capable to simulate real behavior of welded joints in terms of susceptibility to Reheat Crack Phenomena. The test may be performed using a destructive approach on samples obtained directly from the welded joint, after having the samples heat treated and stressed as in the real reactors, in order to simulate as closely as possible the conditions experimented by the real parts of the reactor.

Based on the tests to be discussed later in more details, it is possible to select welding materials that are less susceptible to reheat cracking, optimize the welding parameters (for example heat input, current type, double or single wire, wire diameter, etc.) and optimize the heat treatment parameters using as base material, for example, 2.25 Cr1 Mo 0.25V. Therefore, some of the advantages of one or more exemplary embodiments include producing reactors free from expensive and difficult repairs due to the reheat cracking damage, and achieving a high confidence on the quality of the product, as the reheat cracking flaws are often difficult to identify with non-destructive test after the reactor is built.

The tests proposed in the exemplary embodiments may be performed without interference with the production process, as these tests are "on-line" and can be used every time a change in both the supply of the materials or in the welding parameters and heat input occurs. Also, with these tests it is possible, before starting the production of a reactor, to verify the susceptibility of the materials to reheat cracking and prevent the manufacture of damaged components for the reactors.

Figure 3:
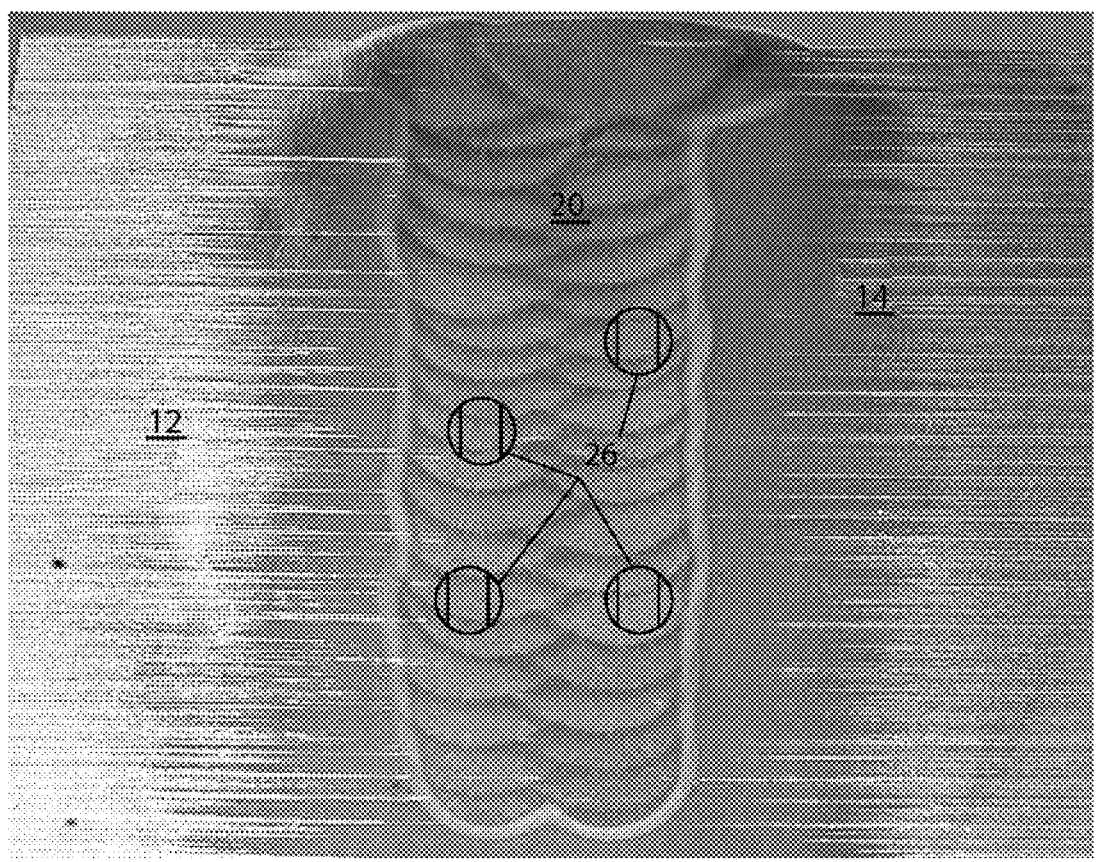
FIG. 3 is an illustration of a welded region according to an exemplary embodiment.
Figure 4:
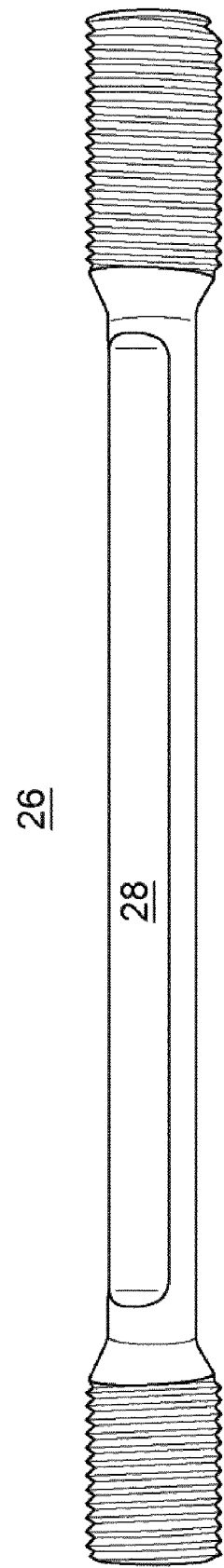
FIG. 4 is a schematic diagram of a sample of the welded region according to an exemplary embodiment.

According to an exemplary embodiment, a sample 26 to be tested is selected from a real welding joint 20 as shown in FIG. 3. The sample 26 may be taken to be entirely from within the welding joint 20. One such sample 26 is illustrated in FIG. 4. The sample 26 shown in FIG. 4 may have a rectangular prism shape. Planar faces of this sample may be used to support strain gauges and/or thermocouples for applying a desired elongation and temperature to the sample. These elements may be connected to a computer interface to be controlled by a computer system. Alternatively, these elements may be controlled by an operator. In addition, outputs of these elements may be collected, either by the computer system or by the operator to provide a database including temperatures and stresses applied to the sample. However, other shapes may also be used. According to an exemplary embodiment, a planar face 28 of the sample 26 shown in FIG. 4 may be parallel with the grain orientation of the material.

Figure 5:
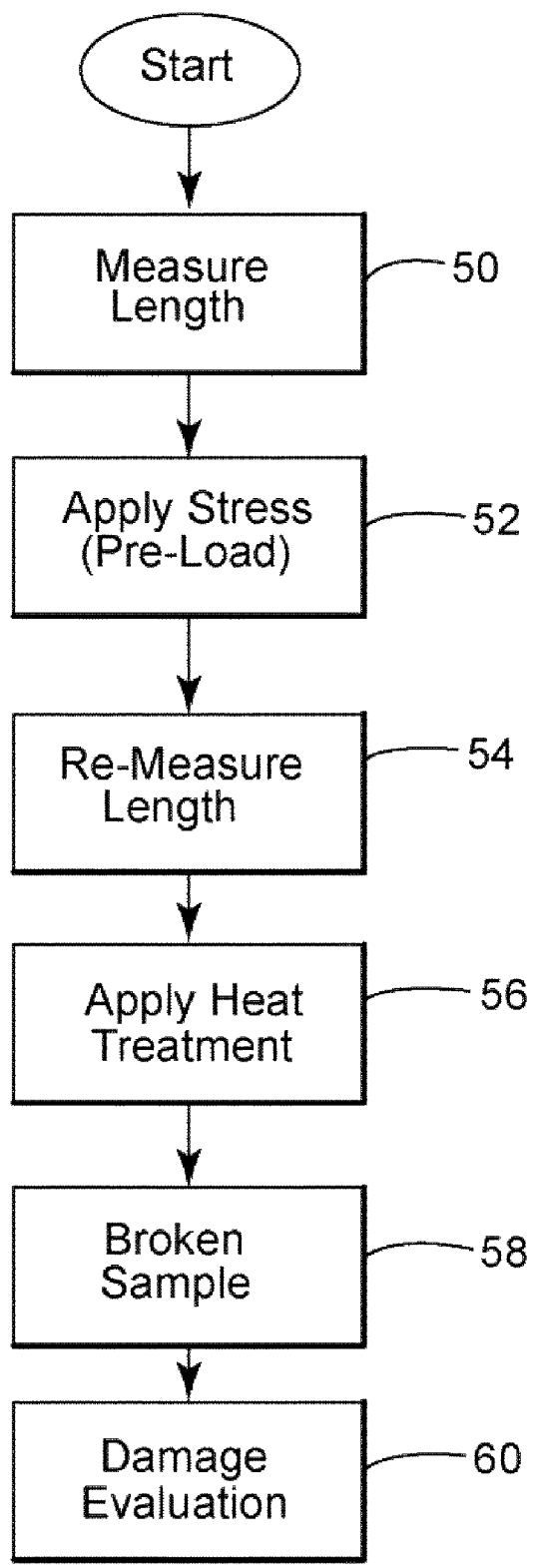
FIG. 5 is a flow chart illustrating steps of a method for determining a susceptibility of reheat cracking of the sample according to an exemplary embodiment.

A procedure for determining the susceptibility to reheat cracking of the sample (probe) is next discussed according to an exemplary embodiment. As shown in FIG. 5, a size of the sample 26 is measured in step 50. The size of the sample 26 may be measured, for example, with a micrometer or with an opto-electronic device that may be controlled by the computer system. The sample may be mounted in, for example, a holder (not shown) that holds the sample. Various mechanical means know by those skilled in the art may be used to fix the sample to the holder such that the sample does not move relative to the holder when a stress is applied by a hydraulic device. The size of the sample may be re-measured after the mechanical means have immobilized the sample into the holder. One of the first or second measurement substeps of step 50 may be omitted in an exemplary embodiment.

A pre-load may be applied to the sample 26 in step 52 by the hydraulic device. The value of the pre-load, which is a load applied before a stress relaxation occurs due to heat treatment, may be close or below a yield strength value of the sample or a residual stress values measured on a real welded component. The yield strength value is specific for each combination of base material and welding material, i.e., the value depends on the welded material included in the sample as the residual stresses depend on the welding process/parameters and on heat treatment applied. According to an exemplary embodiment, the pre-load applied to the sample 26 is such that an elongation of 0.3 to 0.4 mm for this type of sample is achieved. A length of the sample may be in the range of 50 to 500 mm. This elongation is intended to be exemplary and not limit the exemplary embodiments. In fact, this elongation is calculated based on a length of the sample.

After the application of the pre-load, the force applying device is removed from the holder and the length of the sample is re-measured to verify whether the desired elongation value has been obtained. A desired elongation for sample 26 may be from 0.2% to 0.3% of the length of the sample. If the desired elongation value has not been obtained, steps 52 and 54 may be repeated until the desired elongation is achieved. Once the desired elongation has been achieved, the sample is removed from the holder and may be inserted in a heat generating device, for example, an oven, to be heated as will be discussed next.

Figure 6:
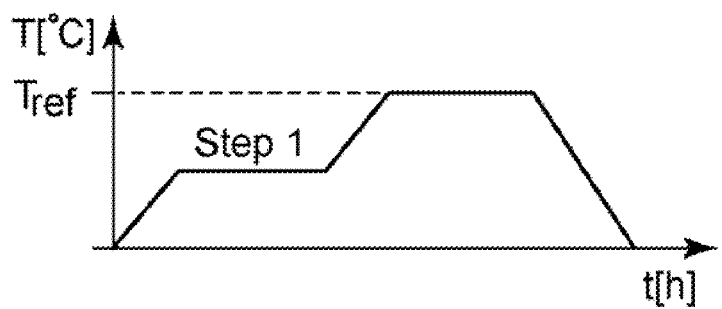
FIGS. 6-8 illustrate various heat treatments that may be applied to the sample according to exemplary embodiments.
Figure 7:
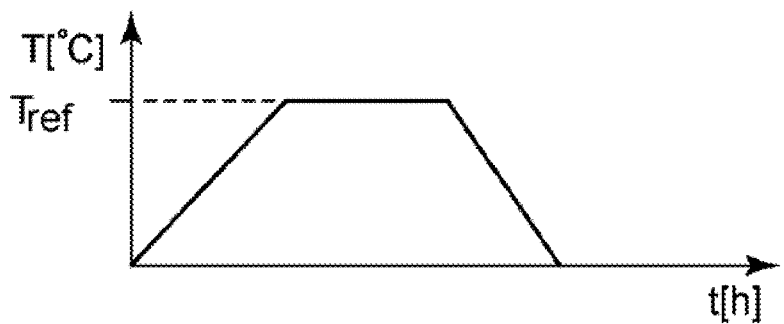
Figure 8:
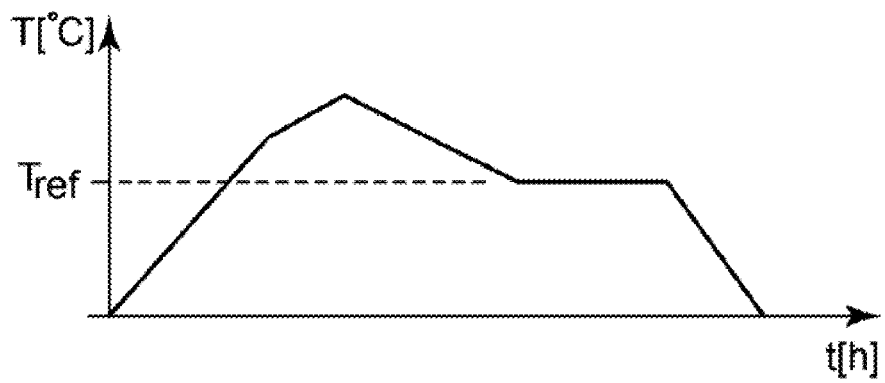

Three different heat treatment profiles may be applied to the sample as discussed next. However, other heat treatment may also be applied and the discussed three heat treatments are not limiting the exemplary embodiment and are also not exhaustive. One of the heat treatment is applied to the sample in step 56. These three heat treatments are illustrated in FIGS. 6-8. FIG. 6 illustrates a heat treatment having a slow ramp with a step I at a critical temperature, FIG. 7 illustrates an intermediate ramp, and FIG. 8 illustrates a double ramp with overshoot. The Tref may be 675 C, the ramps may have a slope between 5 and 20 C/h, the holding portions may extend over 5 to 10 hours, and the critical temperature may be 650 C. However, one of ordinary skill in the art would recognize that these values are exemplary and not applicable to all base materials. These particular values were applied in this exemplary embodiment to the base material of 2.25 Cr 1 Mo 0.25V.

Figure 9:
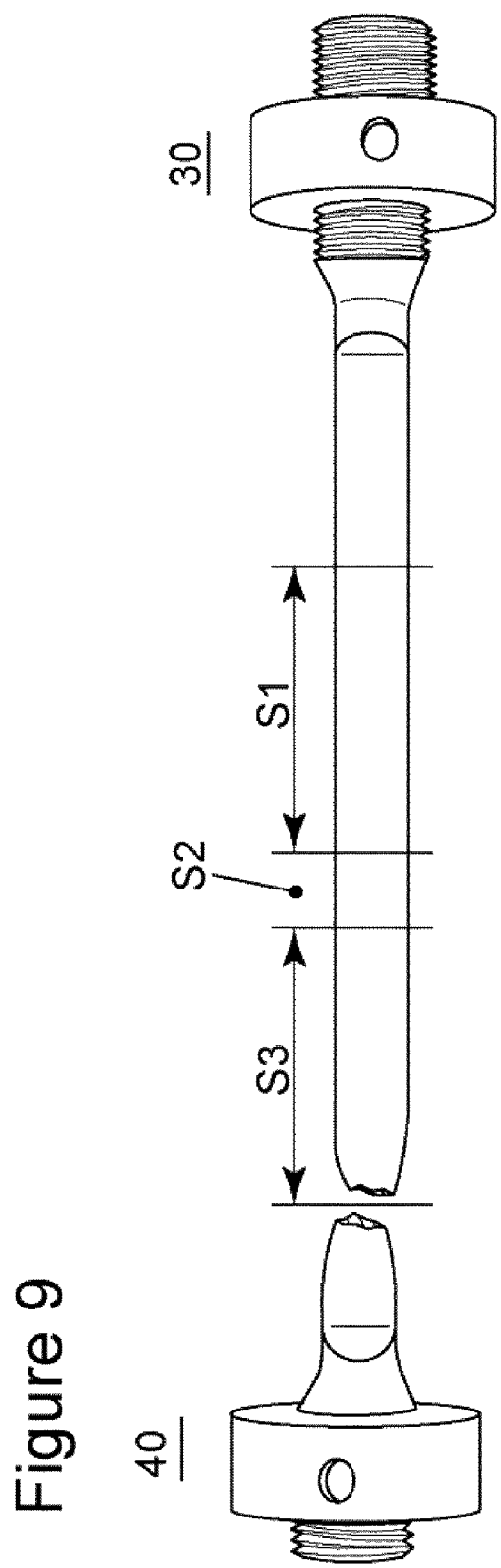
FIG. 9 is a schematic diagram of the broken sample and the sections of the sample analyzed according to an exemplary embodiment.

The length of the sample 26 may be measured again in step 56 and then, another force is applied in step 58 to the sample until the sample is broken. The sample may fracture during the application of this second force in one of a number of ways: by cleavage, by transgranular ductile fracture, by intergranular pure brittle or integranular ductile fracture, or other mechanism. The fracture may occur with the presence of ductility or not. These characteristics are analyzed for the broken sample 26 in step 60 of FIG. 5. According to an exemplary embodiment, three different metallographic sections are considered for each sample. Sections S1 and S3 are longitudinal sections and section S2 is a cross section, as shown in FIG. 9. However, according to another exemplary embodiment, at least two sections are used, i.e., S1 and S2. According to an exemplary embodiment, these three sections are considered on a same portion 30 of sample 26. Various tests are performed on the micrographic surfaces of these sections S1 to S3, as for example, checking reheat cracking damage location on S1 and S3 and checking a type of grain structure on S2. Section 40 of sample 26 shown in FIG. 9 may be used to analyze the fracture surface, as for example, comparing the brittle surface to the ductile surface with the help of a scanning electronic microscope (SEM).

An intergranular fracture is a fracture that follows the grain boundaries of the material. If the material has multiple lattice organizations, when one lattice ends and another begins, the fracture changes direction to follow the new grain. This results in a fairly jagged looking fracture with bumpy edges. The intergranular facture may also be described as similar to cracks that take place along the grain boundary of a material. Straight edges of the grain and shiny surfaces may be seen.

A transgranular fracture is a fracture that follows the edges of lattices in a granular material, ignoring the grains in the individual lattices. This results in a fairly smooth looking fracture with less sharp edges than one that follows the changing grains. Transgranular fractures may be described as similar to wooden jigsaw puzzle pieces with the grains showing, but with each piece having grains running in a different direction. To the contrary, an intergranular fracture follows the edges of the puzzle pieces, ignoring the grains in the wood.

Figure 10:
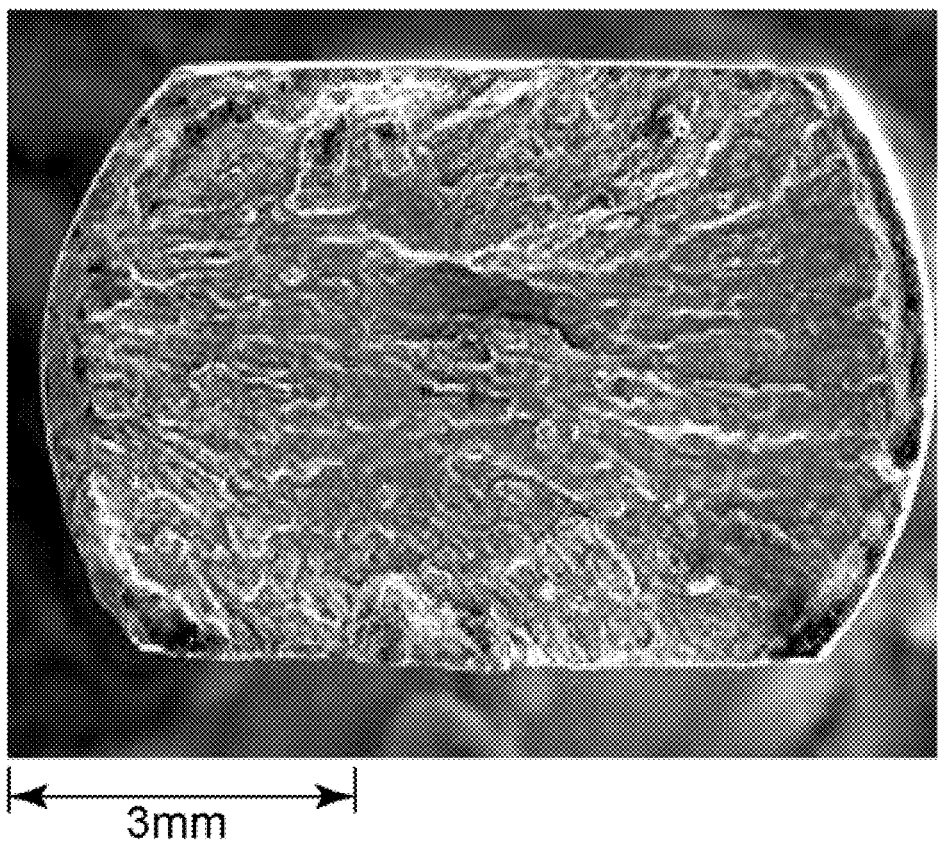
FIGS. 10-12 illustrate various types of fractures that might appear in the sample.
Figure 11:
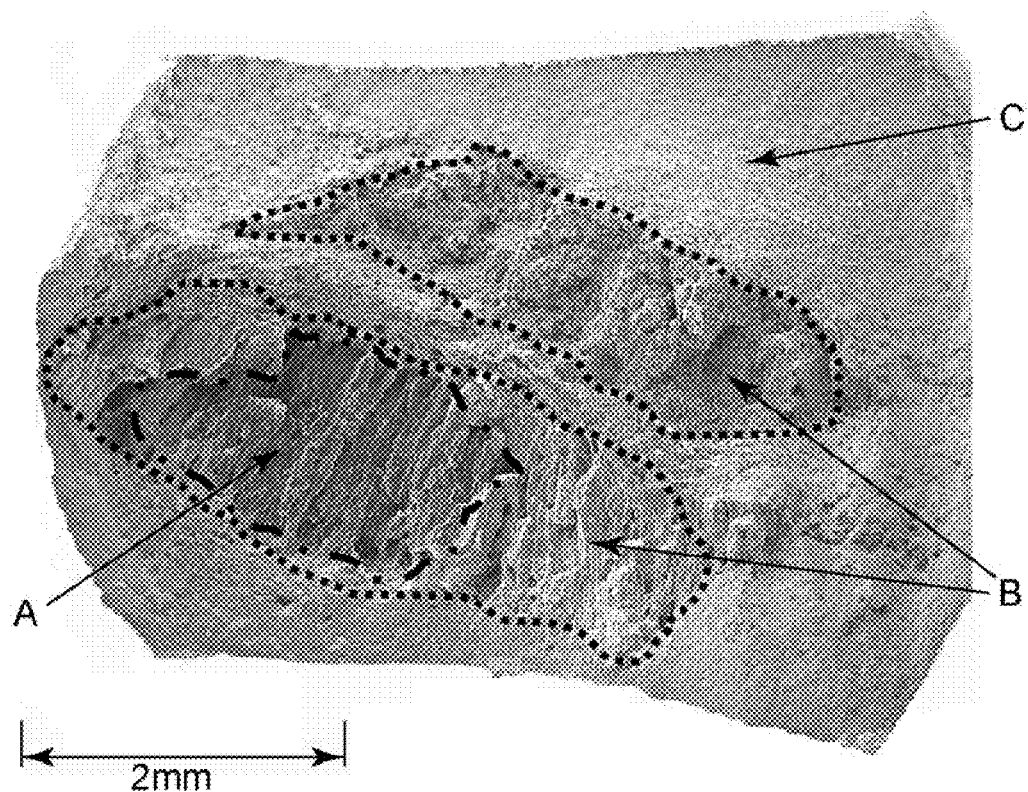
Figure 12:
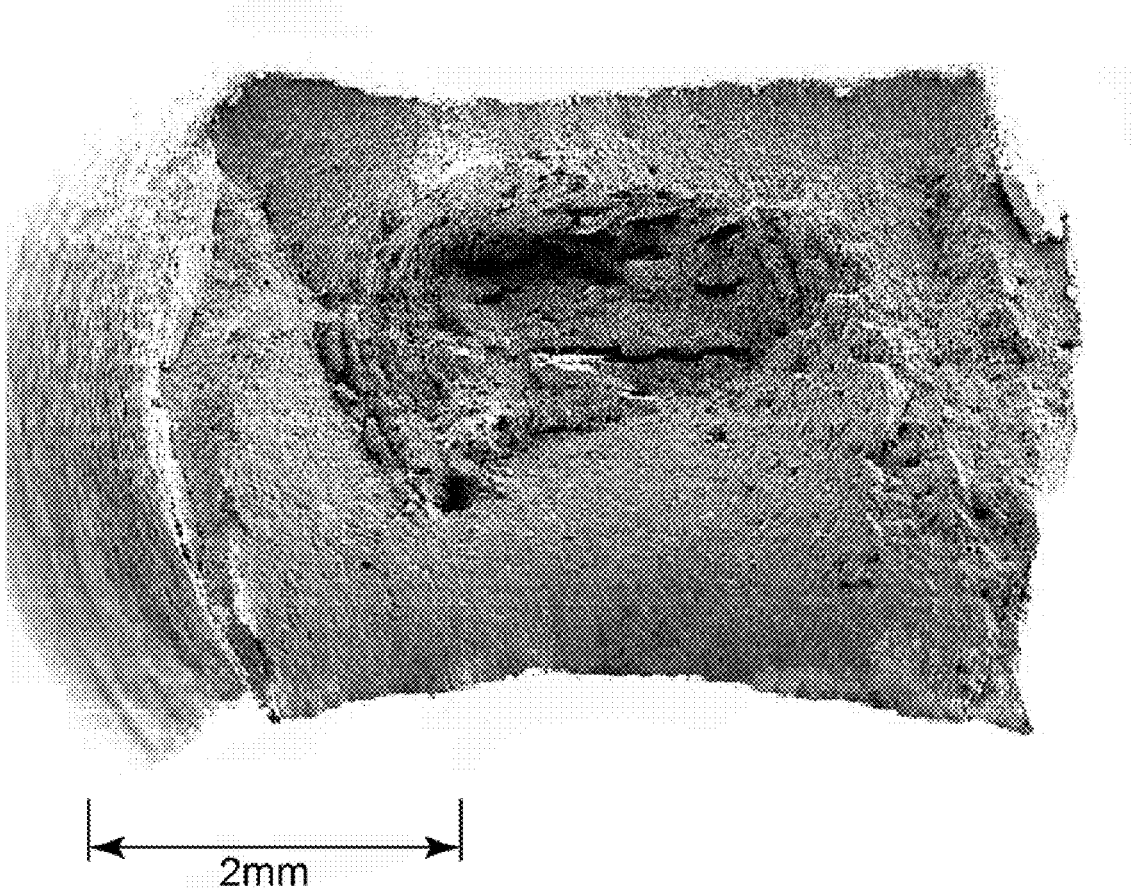

These different types of fractures may be determined by SEM analysis, either performed by an operator or automatically by the computer system discussed above. Various possible fractures are shown in FIGS. 10-12. FIG. 10 shows a fracture surface with 100% intergranular crack damage with no ductility. FIG. 11 shows a fracture surface with a mixture of an area (A) of intergranular crack damage with no ductility, an area (B) of intergranular crack damage with ductility, and an area (C) of transgranular fracture with ductility. FIG. 12 shows a fracture surface with 100% transgranular fracture with ductility.

Figure 13:
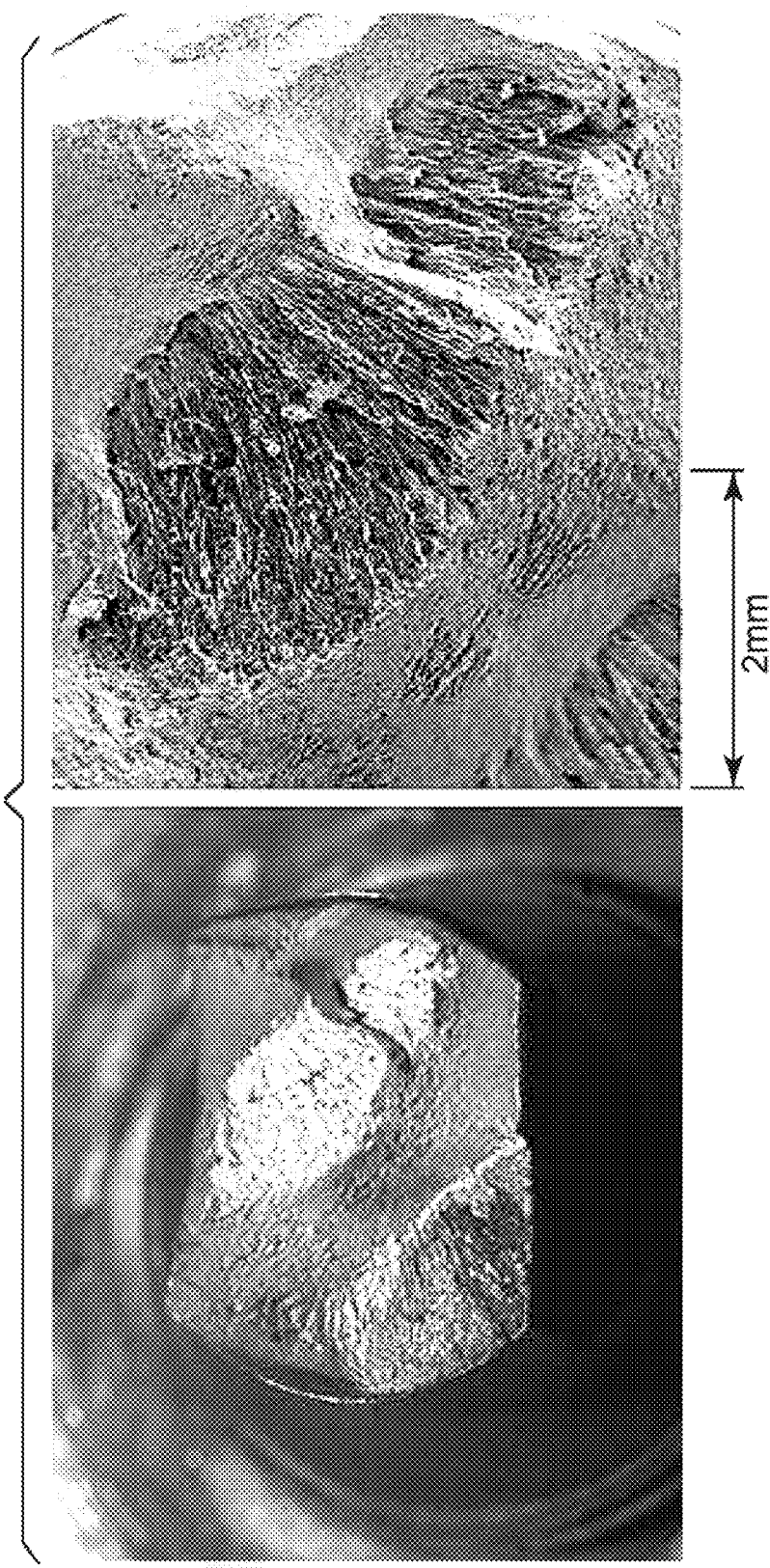
FIGS. 13-16 illustrate test results of the sample according to various exemplary embodiments.
Figure 14:
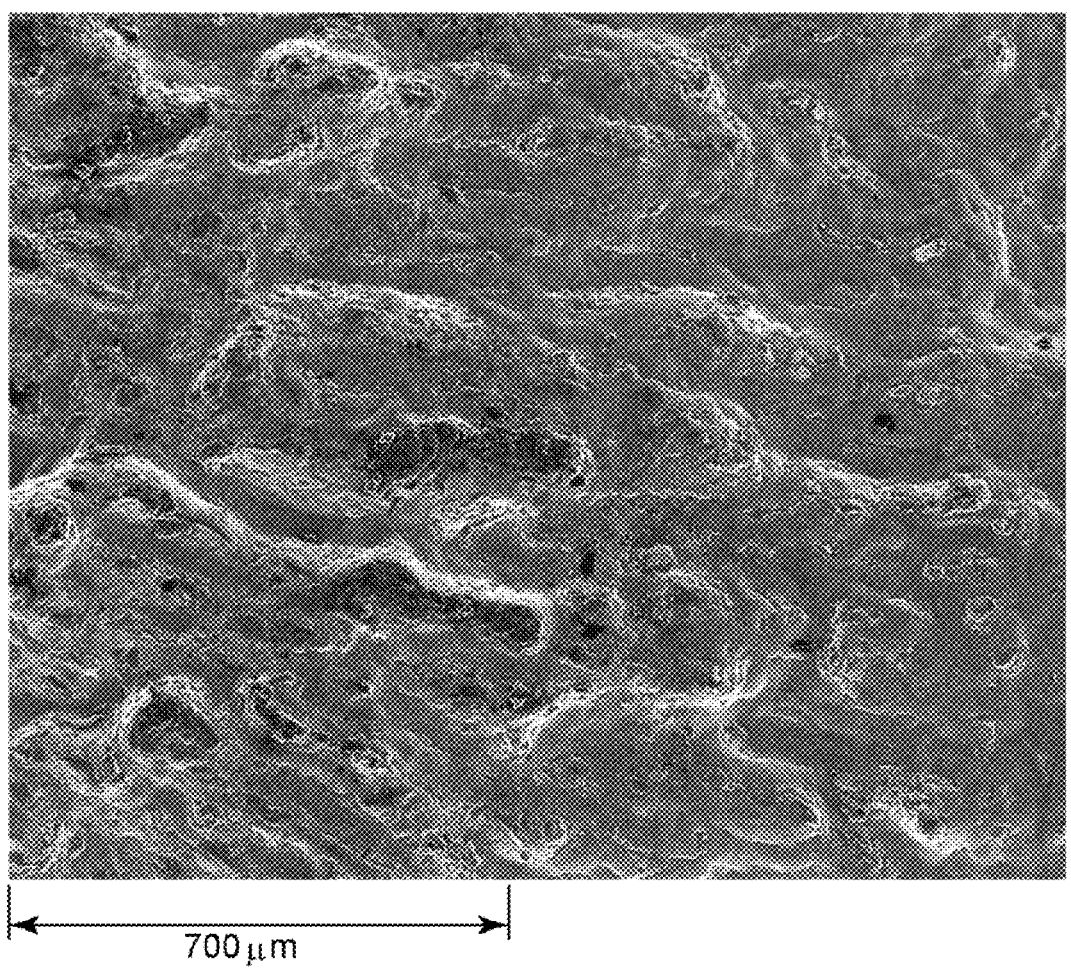
Figure 15:
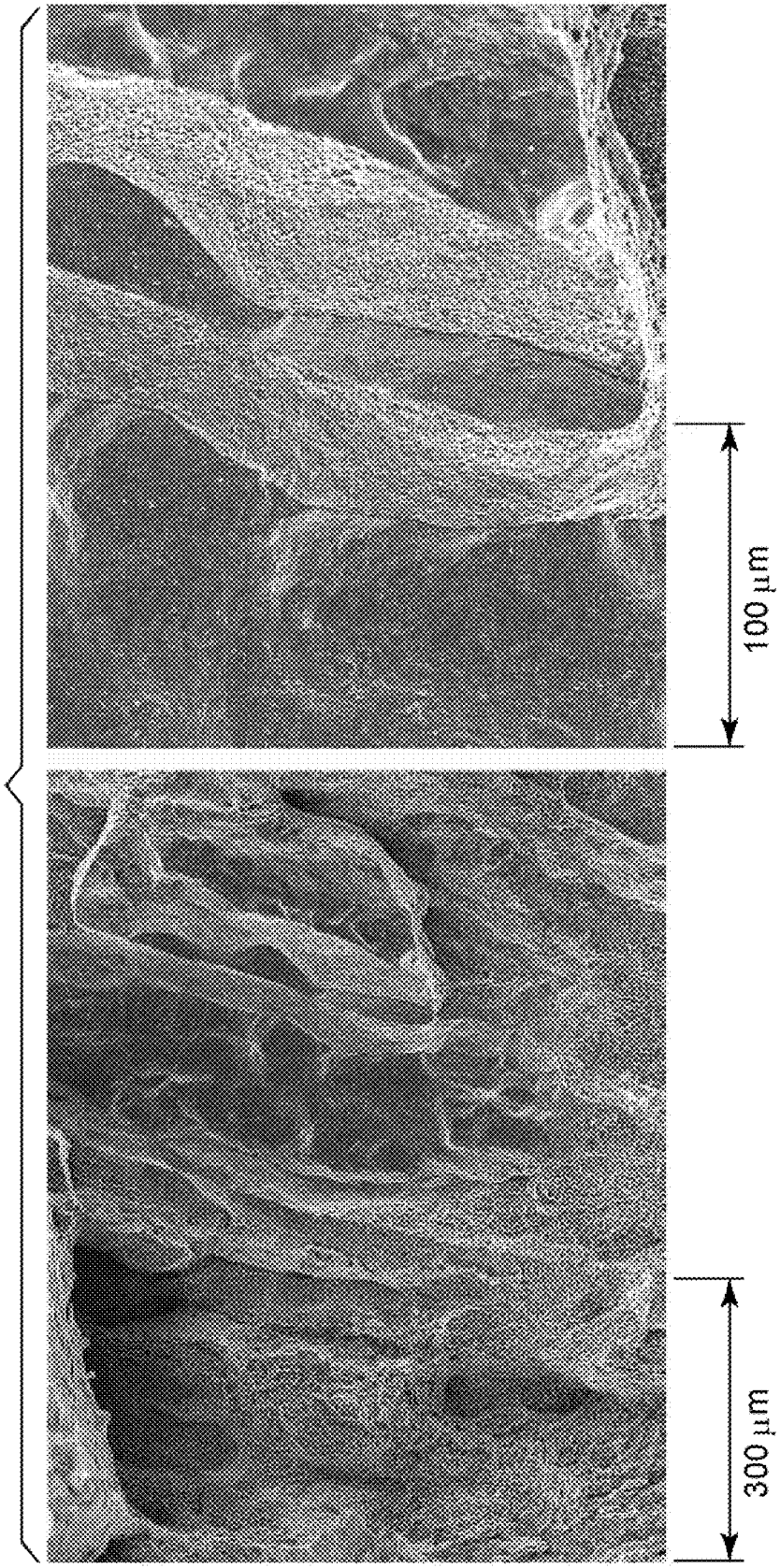
Figure 16:
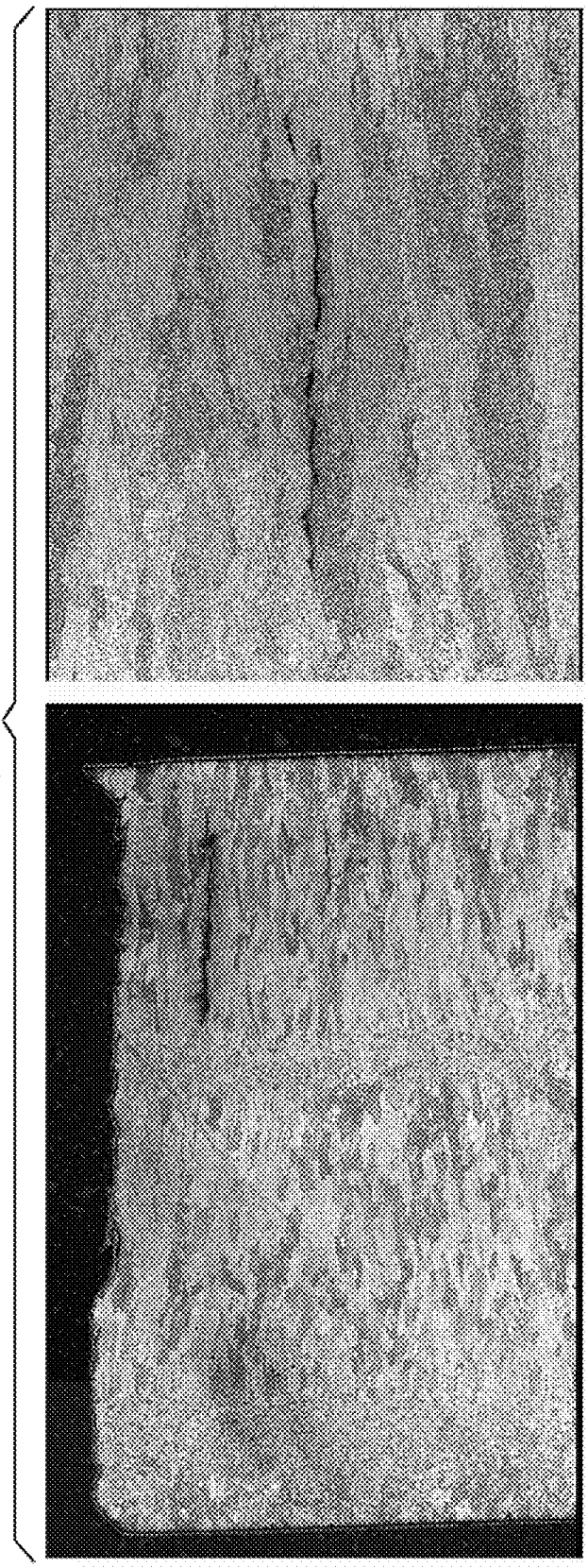

At room temperature, the fracture surface usually presents only transgranular ductility and the presence of intergranular features are indications that some damage occurred at high temperature during the heat treatment and is considered as damage. FIGS. 13-16 illustrates test results of sample 26 according to an exemplary embodiment. FIG. 13 shows intergranular cracks in a fracture surface (cross section). FIG. 14 shows intergranular cracks covered by an oxide layer. FIG. 15 shows a fracture surface with brittle intergranular appearance. FIG. 16 shows micrographic longitudinal sections analyzed by optical microscope, where multiple parallel intergranular cracks below fracture surface and crack propagation at grain boundaries have been detected.

Figure 17:
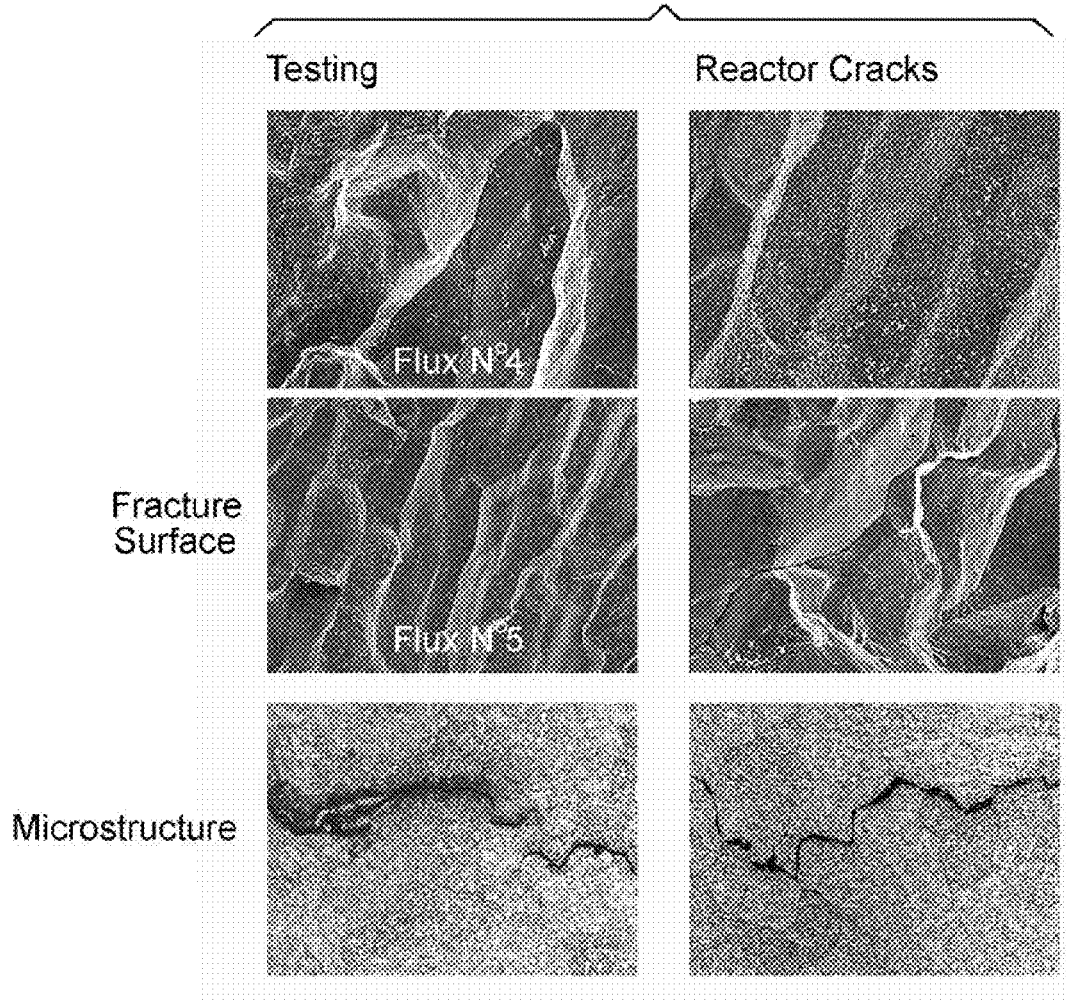
FIG. 17 illustrates a comparison of the fracture surfaces and their microstructures for the tested samples and real reactors.

The results of the tests performed were similar to the real reheating cracks observed in the reactors. The presence of three different microstructures in the samples were identified from the analysis of the samples, (a) fine equiax grain structure (grain are smaller and randomly oriented), (b) coarse equiax grain structure (grains are coarser but still randomly oriented), and (c) columnar grain structure (grains are coarser and directionally oriented). For ensuring the validity of the test, an amount of 45% of coarse grain structure should be present. A comparison of the fracture surfaces and their microstructures for the tested samples and real reactors cracks is shown in FIG. 17. This match between the samples and the reactor cracks indicates that the stresses and heat treatments applied to the samples during the preparation phase, according to the exemplary embodiments, are appropriate, thus demonstrating the ability of the discussed methods to reproduce reheat cracking damage on real components.

In order to quantitatively evaluate the effects of the heat treatments on the sample, according to an exemplary embodiment, a heat treatment severity index (SI) is introduced and calculated for each heat treatment. The severity index may be calculated based on a Creep Damage, on a Creep Strain Accumulation, or other techniques.

According to an exemplary embodiment, the first severity index is calculated for the broken sample based on various temperature profiles that approximate the temperature curve of the heat treatment. More specifically, the real temperature of the heat treatment is approximated with a step temperature curve and the severity index is calculated as a sum of step severity indexes calculated for each step of the step temperature curve.

According to another exemplary embodiment, the second severity index may be calculated based on the same temperature profiles that approximate the temperature curve of the heat treatment. In this regard, a damage parameter of the broken sample is evaluated by approximating a real temperature of the heat treatment with a step temperature curve and calculating the second severity index as a sum of step severity indexes for each step of the step temperature curve.

Figure 18:
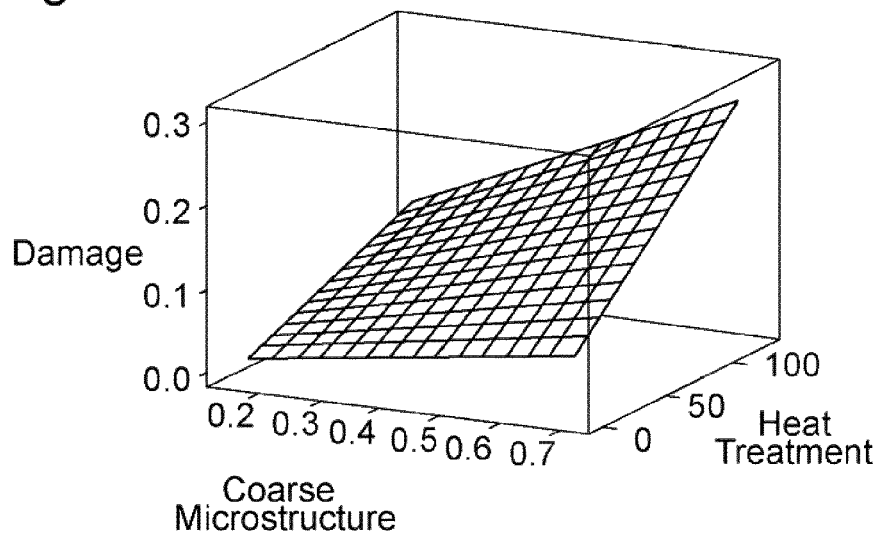
FIGS. 18 and 19 are graphs showing the dependence of the damage to the sample on the heat treatment and coarse microstructure according to exemplary embodiments.
Figure 19:
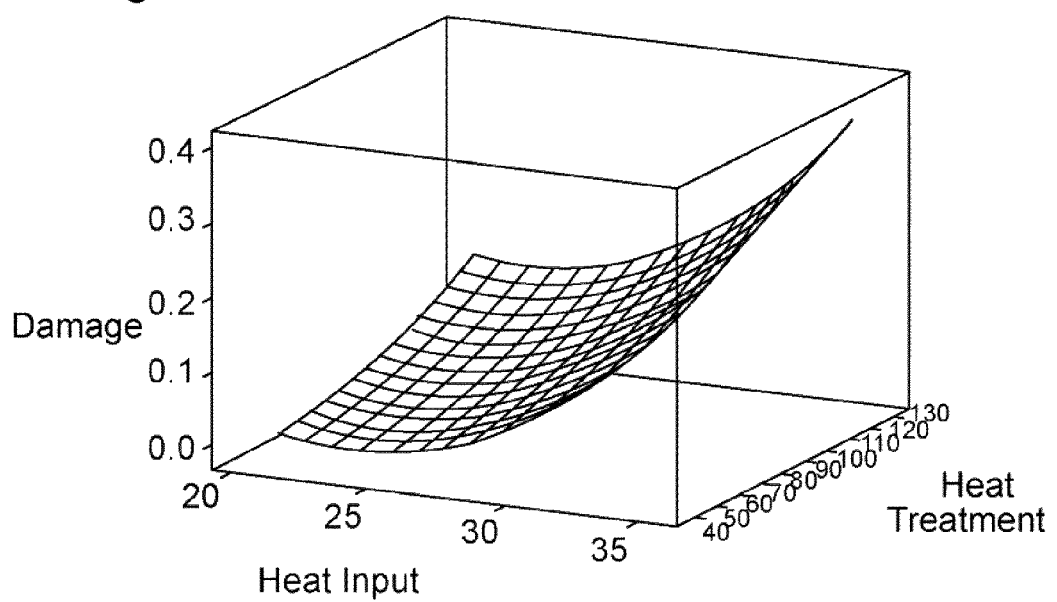

According to an exemplary embodiment, the amount of the damage in the sample is associated with brittle areas and it may be measured by image analysis software. A function of the severity index SI (based on creep damage) and the coarse microstructure of the sample is plotted against amount of damage, as shown in FIG. 18. Based on this figure, it is noted that the damage increases with the severity index of the heat treatment and also with the percentage of coarse grain size. The damage of the sample has also been plotted against the severity index SI (based on creep strain accumulation) and the heat input (thermal energy produced during the welding process) as shown in FIG. 19. Based on this figure, it is noted that the damage increases with the heat input value. However the dependency of damage percentage from the above parameters may be altered, depending of the filler materials (consumables) used during the welding process. In this respect, FIG. 20 shows that several consumables from various suppliers exhibit different percentages of damage.

Figure 20:
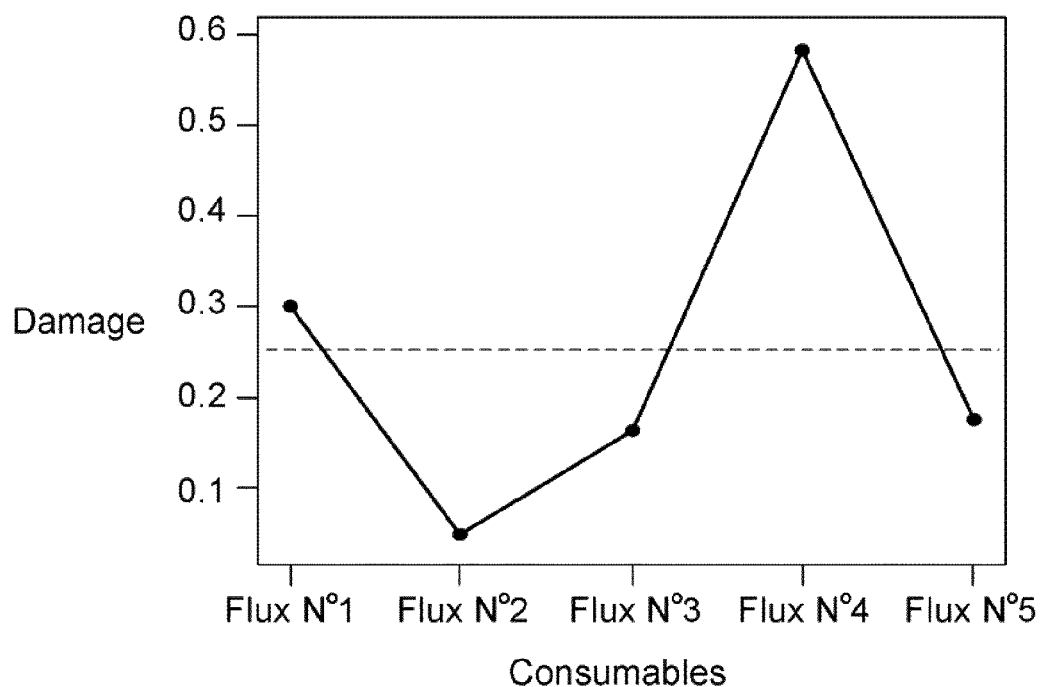
FIG. 20 is a graph showing the dependence of the damage to the sample on consumables according to an exemplary embodiment.

Based on the results summarized in FIGS. 18-20, the present inventors have concluded that the microstructure (in terms of coarse grain size) of the sample contribute to the amount of damage exhibited by the sample. Thus, a reduction in the amount of columnar grain structure improves the chances of the material to resist to the reheat cracking, even if, for appropriate consumables, a high percentage of coarse grain structure does not promote reheat cracking damage. Further, it has been observed that the effect of the consumables may dominate other factors. In this regard, according to an exemplary embodiment, the welding parameters and the heat treatment may have a second order effect compared to the influence of the welding consumables. However, the welding parameters and the heat treatment may mitigate the reheating cracking even though these parameters may be different for different fluxes.

Figure 21:
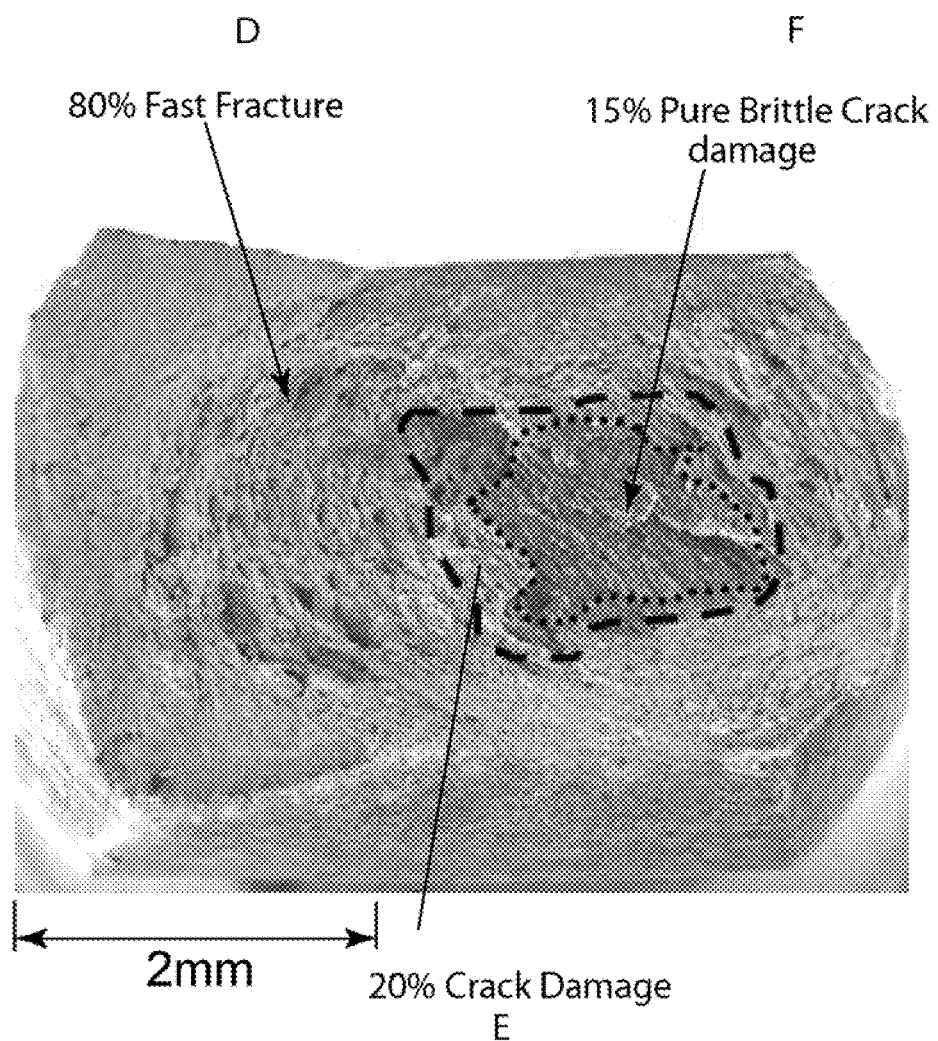
FIG. 21 is a schematic diagram of a fractured surface according to an exemplary embodiment.

According to another exemplary embodiment, the susceptibility of the studied sample to reheat cracking is based on evaluating an area of the brittle surface found in the analyzed sections. For example, as shown in FIG. 21, the fracture surface may show a first area D of fast fracture, which is not related to reheat cracking damage and a second area E of crack damage (intergranular ductile fractographic path) that is produced by reheat crack phenomena. The second area E may include an area F of pure brittle crack damage, which may be substantially 15% of the second area for this example. No ductility fractographic path at grain boundaries has been detected in area F. Such material may be deemed susceptible to reheat cracking if at least one of the following conditions are met: area F is larger than 0% of area E or area E is larger than about 10% of the total fracture surface (area D and E) for the specific sample discussed above. However, these percentages may be different for other materials.

Thus, based on the estimated damage and/or the extent of area E and F discussed with regard to FIG. 21, the susceptibility to reheat cracking of the studied sample is predicted in step 60 (see FIG. 5). If the damage is below a predetermined threshold, the sample is considered to not be susceptible to reheat cracking and the materials used in the sample may be used in mass production. However, if the damage in the sample is above the predetermined threshold, the materials used in the sample are deemed not suitable for a mass production of the reactor. The predetermined threshold is material (consumables) dependent. For the reactor discussed in one of the above exemplary embodiments, i.e., 2.25 Cr 1 Mo 0.25V, the predetermined threshold is 0% for area F and a maximum of 10% of the total fracture surface for area E.

Figure 22:
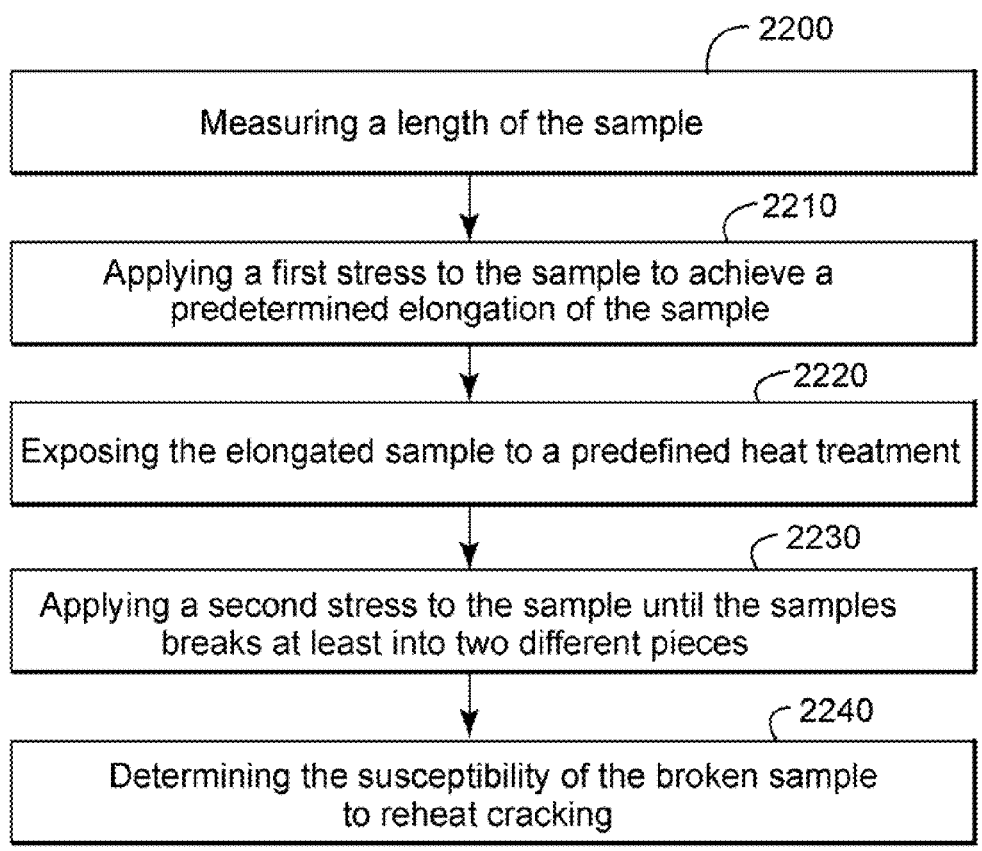
FIG. 22 is a flow chart illustrating steps for determining a susceptibility of a material to reheat cracking according to an exemplary embodiment.

According to an exemplary embodiment illustrated in FIG. 22, there is a method for determining a susceptibility of a sample of at least one material, which includes a welded area, to reheat cracking. The method includes a step 2200 of measuring a length of the sample, a step 2210 of applying a first stress to the sample to achieve a predetermined elongation of the sample, a step 2220 of exposing the elongated sample to a predefined heat treatment, a step 2230 of applying a second stress to the sample until the sample breaks at least into two different pieces, and a step 2240 of determining the susceptibility of the broken sample to reheat cracking.

This method may be implemented in a system that includes a computer system having an interface configured to receive data from, for example, a stress applying and measuring device, a thermocouple, a length measuring device, a SEM microscope, etc. The technical effect of such device or computer instructions that configure the computer system is the determination of the susceptibility of the sample to exhibit reheat cracking.

Figure 23:
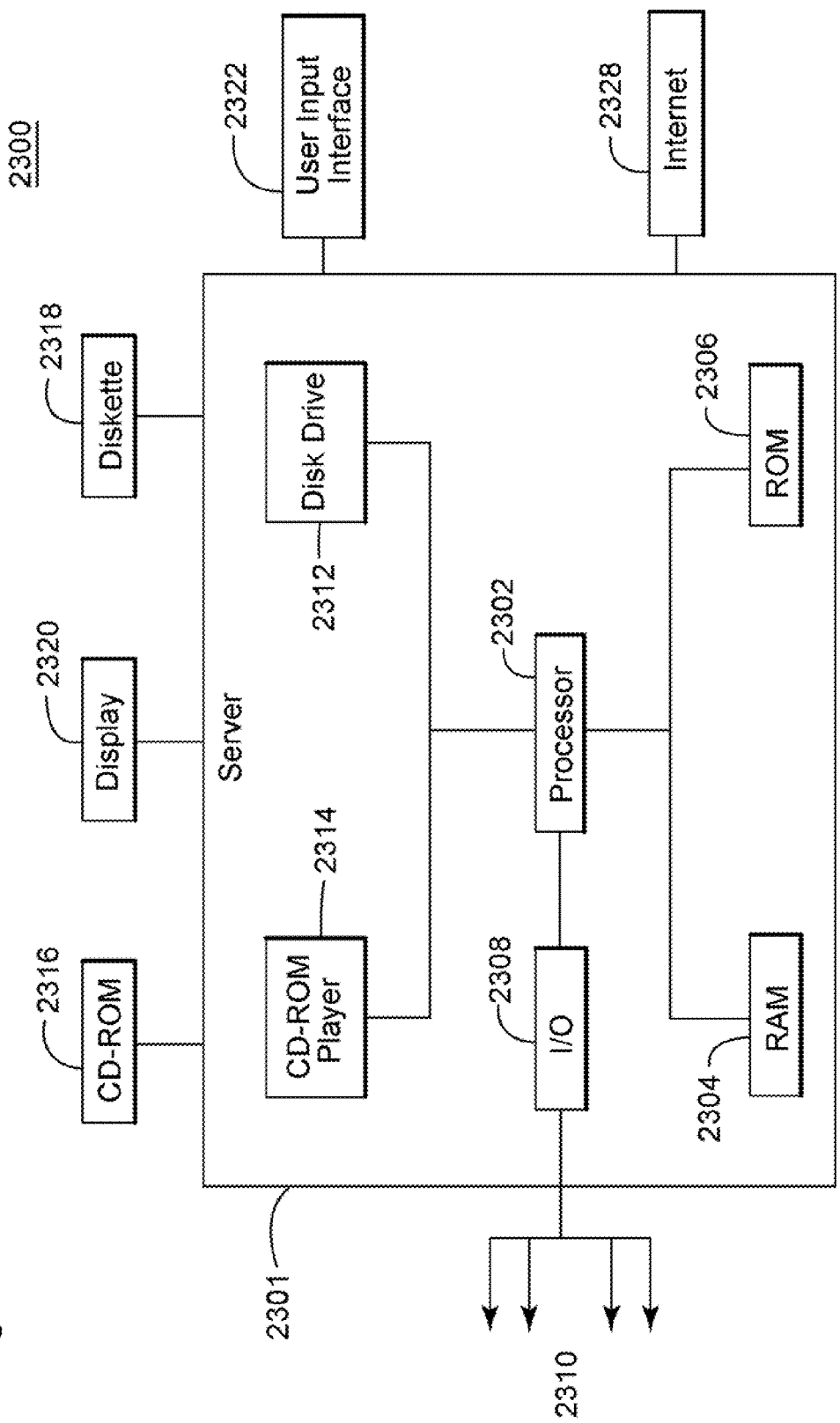
FIG. 23 is a schematic diagram of a computing system.

According to an exemplary embodiment, a computing system may be used to automatically perform the measurements and calculations discussed above in the various exemplary embodiments, measuring the length of the sample, applying the preload and load, applying the heat treatment, and determining the extent of areas E and F. Thus, for purpose of illustration and not of limitation, an example of a representative computing system capable of carrying out operations in accordance with the exemplary embodiments is illustrated in FIG. 23. It should be recognized, however, that the principles of the present exemplary embodiments are equally applicable to standard computing systems. Hardware, firmware, software or a combination thereof may be used to perform the various steps and operations described herein.

The example computing arrangement 2300 suitable for performing the activities described in the exemplary embodiments may include a server 2301. Such a server 2301 may include a central processor (CPU) 2302 coupled to a random access memory (RAM) 2304 and to a read-only memory (ROM) 2306. The ROM 2306 may also be other types of storage media to store programs, such as programmable ROM (PROM), erasable PROM (EPROM), etc. The processor 2302 may communicate with other internal and external components through input/output (I/O) circuitry 2308 and bussing 2310, to provide control signals and the like. The processor 2302 carries out a variety of functions as is known in the art, as dictated by software and/or firmware instructions.

The server 2301 may also include one or more data storage devices, including hard and floppy disk drives 2312, CD-ROM drives 2314, and other hardware capable of reading and/or storing information such as DVD, etc. In one embodiment, software for carrying out the above discussed steps may be stored and distributed on a CD-ROM 2316, diskette 2318 or other form of media capable of portably storing information. These storage media may be inserted into, and read by, devices such as the CD-ROM drive 2314, the disk drive 2312, etc. The server 2301 may be coupled to a display 2320, which may be any type of known display or presentation screen, such as LCD displays, plasma display, cathode ray tubes (CRT), etc. A user input interface 2322 is provided, including one or more user interface mechanisms such as a mouse, keyboard, microphone, touch pad, touch screen, voice-recognition system, etc.

The server 2301 may be coupled to other computing devices, such as the landline and/or wireless terminals and associated watcher applications, via a network. The server may be part of a larger network configuration as in a global area network (GAN) such as the Internet 2328, which allows ultimate connection to the various landline and/or mobile client devices.

The disclosed exemplary embodiments provide a server, a method and a computer program product for identifying the susceptibility of a sample to reheat cracking. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

As also will be appreciated by one skilled in the art, the exemplary embodiments may be embodied in a server, as a method or in a computer program product. Accordingly, the exemplary embodiments may take the form of an entirely hardware embodiment or an embodiment combining hardware and software aspects. Further, the exemplary embodiments may take the form of a computer program product stored on a computer-readable storage medium having computer-readable instructions embodied in the medium. Any suitable computer readable medium may be utilized including hard disks, CD-ROMs, digital versatile disc (DVD), optical storage devices, or magnetic storage devices such a floppy disk or magnetic tape. Other non-limiting examples of computer readable media include flash-type memories or other known memories.

Although the features and elements of the present exemplary embodiments are described in the embodiments in particular combinations, each feature or element can be used alone without the other features and elements of the embodiments or in various combinations with or without other features and elements disclosed herein. The methods or flow charts provided in the present application may be implemented in a computer program, software, or firmware tangibly embodied in a computer-readable storage medium for execution by a general purpose computer or a processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other example are intended to be within the scope of the claims if they have structural elements that do not differ from the literal language of the claims, or if they include equivalent structural elements with insubstantial differences from the literal languages of the claims.

What is claimed is:

1. A method for determining a susceptibility of a sample to reheat cracking, the sample being made of at least one material, which includes a welded area, the method comprising:

measuring a length of the sample;

applying a first stress to the sample to achieve a predetermined elongation of the sample;

exposing the elongated sample to a predefined heat treatment;

applying a second stress to the elongated sample that has been exposed to the predefined heat treatment, until the sample breaks at least into two different pieces; and determining the susceptibility of the broken sample to reheat cracking.

2. The method of claim 1, wherein the step of determining comprises:
   calculating a creep damage severity index for the broken sample based on temperature profiles of the heat treatment; and
   evaluating a damage parameter of the sample based on the calculated creep damage severity index.

3. The method of claim 2, wherein the step of calculating comprises:
   approximating a real temperature of the heat treatment with a step temperature curve; and
   calculating the creep damage severity index as a sum of the severity index for each step of the step temperature curve.

4. The method of claim 1, wherein the step of determining comprises:
   calculating a creep strain accumulation severity index for the broken sample based on temperatures profiles of the heat treatment; and
   evaluating a damage parameter of the sample based on the calculated creep strain accumulation severity index.

5. The method of claim 4, wherein the step of calculating comprises:
   approximating a real temperature of the heat treatment with a step temperature curve; and
   calculating the creep strain accumulation severity index as a sum of the severity index for each step of the step temperature curve.

6. The method of claim 1, wherein the heat treatment is one of:
   a first heat treatment that includes a first region of increasing temperature, a second region of constant temperature, a third region of increasing temperature, a fourth region of constant temperature, and a fifth region of decreasing temperature;
   a second heat treatment that includes a first region of increasing temperature, a second region of constant temperature, and a third region of decreasing temperature; and
   a third heat treatment that includes a first region of increasing temperature with a first slope, a second region of increasing temperature with a second slope, a third region of decreasing temperature with a third slope, a fourth region of constant temperature, and a fifth region of decreasing temperature with a fourth slope.

7. The method of claim 1, further comprising:
   cutting the sample to include only welded material.

8. The method of claim 1, further comprising:
   cutting a face of the sample to be parallel to a grain orientation of the material of the sample.

9. The method of claim 1, further comprising:
   applying on plane surfaces of the sample strain gauges and/or thermocouples to monitor strain and/or temperature of the sample.

10. The method of claim 1, wherein the step of determining further comprises:
    analyzing at least one fracture surface of the broken sample with a scanning electron microscope to identify a first area of crack damage and a second area of fast fracture, wherein the first area of crack damage includes a third area of intergranular pure brittle crack damage; and
    classifying the sample as susceptible to reheat cracking when at least one of the following conditions are met: the third area is higher than about 0% of the first area and the first area of crack damage is higher than about 10% of a total area of the fracture surface of the broken sample, the broken sample having a chemical composition of 2.25 Cr 1 Mo 0.25V.

11. The method of claim 1, wherein the step of determining further comprises:
    analyzing at least a transversal micrographic section to determine the percentage of coarse grain size structure; and
    validating the test when the coarse grain structure in the section is equal or higher than about 45% of the total cross section area.

12. A system for determining a susceptibility of a sample to reheat cracking, the sample being made of at least one material, which includes a welded area, the system comprising:
    an interface configured
        to receive first data from a length measuring device that measures a length of the sample,
        to receive second data from a stress applying and measuring device configured to apply a first stress to the sample to achieve a predetermined elongation of the sample and to determine a stress in the sample,
        to receive third data from a heat applying device configured to expose the elongated sample to a predefined heat treatment, and
        to receive fourth data from the stress applying and measuring device configured to apply a second stress to the elongated sample that has been exposed to the predefined heat treatment until the sample breaks at least into two different pieces; and
    a processor connected to the interface and configured
        to control the length measuring device, the stress applying and measuring device, and the heat applying device, and
        to determine the susceptibility of the broken sample to reheat cracking, based on the first, second, third and fourth data received from the length measuring device, the stress applying and measuring device, and the heat applying device via the interface.

13. The system of claim 12, wherein the processor is configured to:
    calculate a creep damage severity index for the broken sample based on temperature profiles of the heat treatment; and
    evaluate a damage parameter of the sample based on the calculated creep damage severity index.

14. The system of claim 13, wherein the processor is further configured to:
    approximate a real temperature of the heat treatment with a step temperature curve; and
    calculate the creep damage severity index as a sum of the severity index for each step of the step temperature curve.

15. The system of claim 12, wherein the processor is configured to:
    calculate a creep strain accumulation severity index for the broken sample based on temperatures profile of the heat treatment; and
    evaluate a damage parameter of the sample based on the calculated creep strain accumulation severity index.

16. The system of claim 15, wherein the step processor is further configured to:
    approximate a real temperature of the heat treatment with a step temperature curve; and
    calculate the creep strain accumulation severity index as a sum of the severity index for each step of the step temperature curve.

17. The system of claim 12, wherein the heat treatment is one of:
- a first heat treatment that includes a first region of increasing temperature, a second region of constant temperature, a third region of increasing temperature, a fourth region of constant temperature, and a fifth region of decreasing temperature;
- a second heat treatment that includes a first region of increasing temperature, a second region of constant temperature, and a third region of decreasing temperature; and
- a third heat treatment that includes a first region of increasing temperature with a first slope, a second region of increasing temperature with a second slope, a third region of decreasing temperature with a third slope, a fourth region of constant temperature, and a fifth region of decreasing temperature with a fourth slope.

18. The system of claim 12, wherein the processor is further configured to:
- analyze at least one fracture surface of the broken sample with a scanning electron microscope to identify a first area of crack damage and a second area of fast fracture, wherein the first area of crack damage includes a third area of intergranular pure brittle crack damage; and
- classify the sample as susceptible to reheat cracking when at least one of the following conditions are met: the third area is higher than about 0% of the first area and the first area of crack damage is higher than about 10% of a total area of the fracture surface of the broken sample, the broken sample having a chemical composition of 2.25 Cr 1 Mo 0.25V.

19. The system of claim 12, wherein the processor is further configured to:
- analyze at least a transversal micrographic section to determine the percentage of coarse grain size structure; and
- validate the test when the coarse grain structure in the section is equal or higher than about 45% of the total cross section area.

20. A computer readable medium for storing computer executable instructions, wherein the instructions, when executed by a processor, determine the processor to determine a susceptibility of a sample to reheat cracking, the sample being made of at least one material, which includes a welded area, the instructions comprising:
- measuring a length of the sample;
- applying a first stress to the sample to achieve a predetermined elongation of the sample;
- exposing the elongated sample to a predefined heat treatment;
- applying a second stress to the elongated sample that has been exposed to the predefined heat treatment, until the sample breaks at least into two different pieces; and
- determining the susceptibility of the broken sample to reheat cracking.

* * * * *